United States Patent [19]

Takayama et al.

[11] 4,056,622
[45] Nov. 1, 1977

[54] N-SULFONYL-N-DIHALO-PHENYLIMIDAZOLIDINEDIONES

[75] Inventors: Chiyozo Takayama, Osaka; Yoshio Hisada, Kawanishi; Toshiro Kato, Osaka; Akira Fujinami, Hyogo, all of Japan

[73] Assignee: Sumitomo Chemical Company, Limited, Osaka, Japan

[21] Appl. No.: 677,440

[22] Filed: Apr. 15, 1976

[30] Foreign Application Priority Data

Apr. 22, 1975 Japan .................................. 50-49250

[51] Int. Cl.$^2$ ................. C07D 233/86; A61K 31/415
[52] U.S. Cl. .................................. 424/273 R; 548/311
[58] Field of Search ...................... 260/309.5; 424/273

[56] References Cited

U.S. PATENT DOCUMENTS

| | | | |
|---|---|---|---|
| 2,384,964 | 9/1945 | Raiziss et al. | 260/309.5 |
| 3,534,022 | 10/1970 | Umemoto et al. | 260/309.5 |
| 3,668,217 | 6/1972 | Fujinami et al. | 60/309.5 |
| 3,716,552 | 2/1973 | Fujinami et al. | 260/309.5 |

OTHER PUBLICATIONS

Bengelsdorf Chem. Abst. 1954, vol. 48, columns 10010-1.
Fetter et al. Chem. Abst. 1974, vol. 80, No. 3431d.
Joshi et al. Chem. Abst. 1967, vol. 66, No. 115647w.
Dainippon Pharm. Co. Chem. Abst., 1970, vol. 72, No. 31801c.
Umemoto et al. II Chem. Abst. 1971, vol. 74, No. 22839k.

Primary Examiner—Natalie Trousof
Attorney, Agent, or Firm—Connolly and Hutz

[57] ABSTRACT

3-(3',5'-Dihalophenyl)-1-sulfonylimida-zolidine-2,4-diones of the formula:

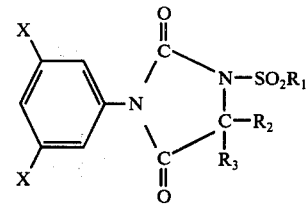

wherein X is a halogen atom, $R_1$ is a $C_1$-$C_{12}$ alkyl group, a $C_2$-$C_4$ alkenyl group or a halogenated $C_1$-$C_4$ alkyl group having 1 to 3 halogen atoms, and $R_2$ and $R_3$ are individually a hydrogen atom or a methyl group, which show high microbicidal activities against various fungi and bacteria without any material toxicity to mammals and which plants and can be produced by reacting the corresponding 1-unsubstituted compound with a sulfonyl halide.

16 Claims, No Drawings

N-SULFONYL-N-DIHALOPHENYLIMIDAZOLI-DINEDIONES

The present invention relates to N'-sulfonyl-N''-dihalophenylimidazolidinediones. More particularly, this invention pertains to 3-(3',5'-dihalophenyl)-1-sulfonylimidazolidine-2,4-diones (hereinafter referred to as "1-sulfonylimidazolidinedione(s)") of the formula:

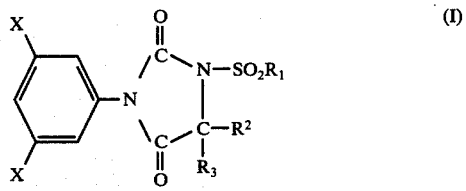

wherein X is a halogen atom such as chlorine or bromine, $R_1$ is a $C_1$–$C_{12}$ alkyl group or a $C_3$–$C_4$ alkyl group, a $C_2$–$C_4$ alkenyl group or a halogenated $C_1$–$C_4$ alkyl group having 1 to 3 halogen atoms, such as a monohalogenated $C_3$–$C_4$ alkyl group, and $R_2$ and $R_3$ are individually a hydrogen atom or a methyl group, and their preparation and use.

The 1-sulfonylimidazolidinediones (I), which are all novel, have now been found to possess strong and broad microbiocidal activities. It is particularly notable that they are much superior to known compounds closely related thereto in chemical structure with respect to the transferability in plant bodies and the preventive effect on the development of infectious spots.

The 1-sulfonylimidazolidinediones (I) have prominent effects on such a wide scope of fungi as *Pyricularia oryzae, Cochliobolus miyabeanus, Pellicularia sasakii, Xanthomonas oryzae, Sclerotinia sclerotiorum, Sclerotinia cinerea, Botrytis cinerea, Alternaria mali, Sclerotinia mali, Sphaerotheca fuliginea, Alternaria kikuchiana, Pellicularia filamentosa* and *Xanthomonas citri.* They can control simultaneously two or more of said fungi and are quite excellent as phytopathogenic microbe-controlling agents. Also, they can effectively control *Aspergillus niger* which propagates in industrial products and hence are excellent as industrial microbicides. Advantageously, they are of extremely low toxicity and have little detrimental actions on mammals and fishes.

A main object of the present invention is to provide novel 1-sulfonylimidazolidinediones (I), which are useful as microbicides. Another object of this invention is to provide a process for producing such 1-sulfonylimidazolidinediones (I). A further object of the invention is to provide microbicidal compositions containing such 1-sulfonylimidazolidinediones (I). These and other objects and advantages of the invention will become apparent from the foregoing and subsequent descriptions.

The 1-sulfonylimidazolidinediones (I) can be prepared by reacting the corresponding 1-unsubstituted compound of the formula:

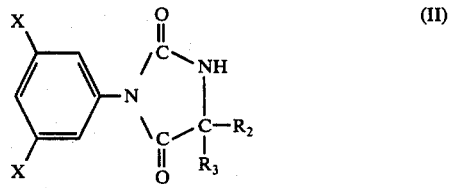

wherein X, $R_2$ and $R_3$ are each as defined above, with a sulfonyl halide of the formula:

$$R_1SO_2Y \qquad (III)$$

wherein $R_1$ is as defined above, and Y is a halogen atom.

The reaction is usually carried out by stirring a mixture of the starting 1-unsubstituted compound (II) with an equivalent or excessive molar amount of the sulfonyl halide (III) at room temperature (0° – 35° C) in the presence or absence of an inert solvent (e.g. benzene, toluene, xylene, tetrahydrofuran, dioxane, chlorobenzene, chloroform, carbon tetrachloride, nitrobenzene). When desired, the reaction may be performed while heating (up to reflux) and/or in the presence of a dehydrohalogenating agent (e.g. pyridine, triethylamine, N-methylmorpholine, dimethylaniline, diethylaniline, sodium hydride, sodium amide, sodium methoxide, sodium ethoxide) so as to accomplish the production of the objective compound smoothly.

The starting 1-unsubstituted compound (II) is obtainable, for instance, by the process as described in German Offenlegungsschrift No. P. 19 58 183.0. Examples of such 1-unsubstituted compound (II) include:

1. 3-(3',5'-Difluorophenyl)imidazolidine-2,4-dione;
2. 3-(3',5'-Dichlorophenyl)imidazolidine-2,4-dione;
3. 3-(3',5'-Dibromophenyl)imidazolidine-2,4-dione;
4. 3-(3',5'-Diiodophenyl)imidazolidine-2,4-dione;
5. 3-(3',5'-Dichlorophenyl)-5-methylimidazolidine-2,4-dione;
6. 3-(3',5'-Dichlorophenyl)-5,5-dimethylimidazolidine-2,4-dione;
7. 3-(3',5'-Dichlorophenyl)-5-methyl-5-ethylimidazolidine-2,4-dione;
8. 3-(3',5'-Dichlorophenyl)-5,5-diethylimidazolidine-2,4-dione;
9. 3-(3',5'-Dichlorophenyl)-5-n-propylimidazolidine-2,4-dione;
10. 3-(3',5'-Dichlorophenyl)-5-methyl-5-n-propylimidazolidine-2,4-dione;
11. 3-(3',5'-Dichlorophenyl)-5-ethyl-5-n-propylimidazolidine-2,4-dione;
12. 3-(3',5'-Dibromophenyl)-5-methylimidazolidine-2,4-dione;
13. 3-(3',5'-Dibromophenyl)-5-ethyl-5-n-propylimidazolidine-2,4-dione;
14. 3-(3',5'-Dibromophenyl)-5,5-dimethylimidazolidine-2,4-dione;
15. 3-(3',5'-Diiodophenyl)-5-methylimidazolidine-2,4-dione;
16. 3-(3',5'-Diiodophenyl)-5-methyl-5-ethylimidazolidine-2,4-dione;
17. 3-(3',5'-Diiodophenyl)-5-methyl-5-isopropylimiazolidine-2,4-dione;
18. 3-(3',5'-Difluorophenyl)-5-methylimidazolidine-2,4-dione;
19. 3-(3',5'-Difluorophenyl)-5,5-dimethylimidazolidine-2,4-dione, and
20. 3-(3',5'-Difluorophehyl)-5,5-diethylimidazolidine-2,4-dione, etc.

Examples of the sulfonyl halide (III) are as follows:
21. Methylsulfonyl chloride;
22. Ethylsulfonyl chloride;
23. n-Propylsulfonyl chloride;
24. Isopropylsulfonyl chloride;
25. n-Butylsulfonyl chloride;
26. Isobutylsulfonyl chloride;
27. sec.-Butylsulfonyl chloride;

28. t-Butylsulfonyl chloride;
29. n-Amylsulfonyl chloride;
30. Isoamylsulfonyl chloride;
31. n-Octylsulfonyl chloride;
32. n-Decylsulfonyl chloride;
33. n-Dodecylsulfonyl chloride;
34. n-Eicosylsulfonyl chloride;
35. Ethylsulfonyl bromide;
36. n-Propylsulfonyl bromide;
37. n-Butylsulfonyl bromide;
38. Isobutylsulfonyl bromide;
39. n-Hexylsulfonyl bromide;
40. n-Decylsulfonyl bromide;
41. Vinylsulfonyl chloride;
42. Allylsulfonyl chloride;
43. Methallylsulfonyl chloride;
44. Allylsulfonyl bromide;
45. Monochloromethylsulfonyl chloride;
46. Dichloromethylsulfonyl chloride;
47. Trichloromethylsulfonyl chloride;
48. Monofluoromethylsulfonyl chloride;
49. β-Chloroethylsulfonyl chloride;
50. β,β-Dichloroethylsulfonyl chloride;
51. γ-Chloropropylsulfonyl chloride;
52. δ-Chlorobutylsulfonyl chloride, etc.

In actual application as microbicides, the 1-sulfonylimidazolidinediones (I) may be used alone without incorporation of any other ingredients such as carriers and diluents or, for easier application, in admixture with such solid carriers or diluents as talc, clay and the like or with such liquid carriers or diluents as organic solvents and the like. The microbicidal compositions can be formulated into any of the ordinarily adopted forms such as, for example, dusts, wettable powders, oil sprays, aerosols, tablets, emulsifiable concentrates and granules.

Further, the 1-sulfonylimidazolidinediones (I) may be used in admixture with other chemicals such as, for example, Blasticidin S, Kasugamycin, Polyoxin, acetylene dicarboximide, 3-[2-(3,5-dimethyl-2-oxocyclohexyl)-2-hydroxyethyl]glytarimide, steptomycin, griseofluvin, pentachloronitrobenzene, pentachlorophenol, hexachlorobenzene, pentachlorobenzyl alcohol, pentachlorobenzaldoxime, 2,6-dichloro-4-nitroaniline, zinc ethylene bisdithiocarbamate, zinc dimethyl thiocarbamate, manganese ethylene bisdithiocarbamate, bis(dimethylthiocarbamoyl) disulfide, 2,4,5,6-tetrachloroisophthalonitrile, 2,3-chloro-1,4-naphthoquinone, tetrachloro-p-benzoquinone, p-dimethylaminobenzenediazo sodium sulfonate, 2-(1-methylheptyl)-4,6-dinitrophenyl crotonate, 2-heptadecylimidazoline acetate, 2,4-dichloro-6-(o-chloroanilino)-S-triazine, dodecylguanidine acetate, (6-methyl-2,3-quinoxalinedithiol cyclic-S,S-dithiocarbonate, 2,3-quinoxalinedithiol cyclic trithiocarbonate, N-trichloromethylthio-4-cyclohexene-1,2-dicarboximide, N-(1,1,2,2-tetrachloroethylthio)-4-cyclohexene-1,2-dicarboximide, N-(3′,5′-dichlorophenyl) maleinimide, N-(3′,5′-dichlorophenyl) succinimide, N-(3′,5′-dichlorophenyl) itaconimide, 3-(3′,5′-dichlorophenyl)-5,5-dimethyloxazolidine-2,4-dione, 2,3-dihydro-5-carboxanilide-6-methyl-1,4-oxazine-4,4-dioxide, 2,3-dihydro-5-carboxanilide-6-methyl-1,4-oxazine, 1-(N-n-butylcarbamoyl)-2-methoxycarbonylaminobenzimidazole, O,O-diethyl-S-benzyl phosphorothioate, O-ethyl-S,S-diphenyl phosphorodithioate, O-ethyl-O-phenyl-O-(2,4,5-trichlorophenyl) phosphate, O,O-dimethyl-O-(3-methyl-4-nitrophenyl) phosphorothioate, S-[1,2-bis(ethoxycarbonyl)ethyl]-O,O-dimethyl phosphorodithioate, O,O-dimethyl-S-(N-methylcarbamoylmethyl) phosphorodithioate, O,O-diethyl-O-(2-isopropyl-6-methyl-4-pyrimidyl) thiophosphate, 3,4-dimethylphenyl-N-methylcarbamate, iron methylarsonate, 2-chloro-4,6-bis(ethylamino)-S-triazine, 2,4-dichlorophenoxyacetic acid (including its salts and esters), 2-methyl-4-chlorophenoxyacetic acid (including its salts and esters), 2,4-dichlorophenyl-4′-nitrophenyl ether, sodium pentachlorophenolate, N-(3,4-dichlorophenyl) propionamide, 3-(3′,4′-dichlorophenyl)-1,1-dimethylurea, α,α,α-trifluoro-2,6-dinitro-N,N-di-n-propyl-p-toluidine, 2-chloro-2′,6′-diethyl-N-(methoxymethyl) acetamide, 1-naphthyl-N-methylcarbamate, methyl-N-(3,4-dichlorophenyl) carbamate, 4-chlorobenzyl-N,N-dimethylthiol carbamate, N,N-diallyl-2-chloroacetamide, ethyl-β-(2,4-dichlorophenoxy) acrylate and cyclohexyl-β-(2,4-dichlorophenoxy) acrylate; and, in every case, no controlling effects of individual chemicals are decreased. Accordingly, simultaneous control of two or more pets and injurious insects is possible. In addition thereto, they may be used in admixture with such agricultural chemicals as insecticides and muticides and with fertilizers.

Practical and presently preferred embodiments of the present invention are illustratively shown in the following examples, wherein parts and % by weight.

EXAMPLE 1

Preparation of the 1-sulfonylimidazolidinediones (I)

Procedure A.

A mixture of 0.05 mole of the 1-unsubstituted compound (II) and 0.1 mole of triethylamine is dissolved in 100 ml of toluene, and 0.06 mole of the sulfonyl halide (III) is dropwise added thereto with stirring at room temperature. The resulting mixture is stirred at room temperature for 6 hours. After the completion of the reaction, the excess of the sulfonyl halide (III), triethylamine and toluene are removed by evaporation, and the residue is washed several times with water and dried to give the 1-sulfonylimidazolidinedione (I). If necessary, the product may be recrystallized from ethanol for purification.

Procedure B 0.05 Mole of sodium hydride is dissolved in 100 ml of tetrahydrofuran, and a solution of 0.05 mole of the 1-unsubstituted compound (II) in 120 ml of tetrahydrofuran is dropwise added thereto with stirring at room temperature. The resulting mixture is stirred for a while, and then 0.06 mole of the sulfonyl halide (III) is dropwise added thereto with stirring at room temperature. Heating with reflux is continued for 7 hours. After the completion of the reaction, the excess of the sulfonyl halide (III) and tetrahydrofuran are removed by evaporation, and the residue is washed several times with water and dried to give the 1-sulfonylimidazolidinedione (I). If necessary, the product may be recrystallized from ethanol for purification.

Examples of the 1-sulfonylimidazolidinedione (I) produced by the above procedure (A) or (B) are shown in Table 1.

Table 1

| Starting Materials | | | | Produced 1-sulfonylimidazolidinedione (I) | | | | | | | |
|---|---|---|---|---|---|---|---|---|---|---|---|
| 1-Unsubstituted compound (II) | Sulfonyl halide (III) | Procedure | No. | Chemical structure | Physical constant | Yield (%) | C | H | N | S | Halogen |
| | | | | | | | \multicolumn{5}{l}{Elementary analysis (%)} |
| 2 | 21 | A | 53 | 3,5-Cl$_2$-C$_6$H$_3$-N(CO-CH$_2$-CO)N-SO$_2$CH$_3$ | M.P., 224.0–225.0° C | 80 | 37.17 (37.32) | 2.50 (2.63) | 8.67 (8.69) | 9.92 (10.01) | (Cl) 21.94 (22.01) |
| 2 | 22 | A | 54 | 3,5-Cl$_2$-C$_6$H$_3$-N(CO-CH$_2$-CO)N-SO$_2$C$_2$H$_5$ | M.P., 200.0–202.0° C | 83 | 39.18 (39.46) | 2.99 (3.14) | 8.31 (8.23) | 9.51 (9.41) | (Cl) 21.03 (20.94) |
| 2 | 23 | A | 55 | 3,5-Cl$_2$-C$_6$H$_3$-N(CO-CH$_2$-CO)N-SO$_2$-n-C$_3$H$_7$ | M.P., 163.0–164.0° C | 87 | 41.04 (41.17) | 3.44 (3.51) | 7.98 (7.95) | 9.13 (9.28) | (Cl) 20.19 (20.19) |
| 2 | 24 | A | 56 | 3,5-Cl$_2$-C$_6$H$_3$-N(CO-CH$_2$-CO)N-SO$_2$-i-C$_3$H$_7$ | M.P., 183.0–184.0° C | 83 | 41.04 (41.24) | 3.44 (3.70) | 7.98 (7.79) | 9.13 (8.95) | (Cl) 20.19 (20.18) |
| 2 | 25 | A | 57 | 3,5-Cl$_2$-C$_6$H$_3$-N(CO-CH$_2$-CO)N-SO$_2$-n-C$_4$H$_9$ | M.P., 149.0–151.0° C | 91 | 42.75 (42.82) | 3.86 (3.91) | 7.67 (7.70) | 8.78 (8.66) | (Cl) 19.41 (19.61) |
| 2 | 26 | A | 58 | 3,5-Cl$_2$-C$_6$H$_3$-N(CO-CH$_2$-CO)N-SO$_2$-i-C$_4$H$_9$ | M.P., 156.5–158.5° C | 80 | 42.75 (42.76) | 3.86 (3.87) | 7.67 (7.72) | 8.78 (8.69) | (Cl) 19.41 (19.35) |
| 2 | 27 | A | 59 | 3,5-Cl$_2$-C$_6$H$_3$-N(CO-CH$_2$-CO)N-SO$_2$-sec.-C$_4$H$_9$ | M.P., 152.5–153.5° C | 82 | 42.75 (42.92) | 3.86 (3.86) | 7.67 (7.57) | 8.78 (8.57) | (Cl) 19.41 (19.31) |
| 2 | 28 | A | 60 | 3,5-Cl$_2$-C$_6$H$_3$-N(CO-CH$_2$-CO)N-SO$_2$-t-C$_4$H$_9$ | M.P., 160.0–163.0° C | 74 | 42.75 (43.01) | 3.86 (3.93) | 7.67 (7.55) | 8.78 (8.54) | (Cl) 19.41 (19.52) |
| 2 | 29 | A | 61 | 3,5-Cl$_2$-C$_6$H$_3$-N(CO-CH$_2$-CO)N-SO$_2$-n-C$_5$H$_{11}$ | M.P., 133.5–134.5° C | 89 | 44.34 (44.05) | 4.25 (4.20) | 7.39 (7.44) | 8.45 (8.28) | (Cl) 18.70 (18.64) |

Table 1-continued

| Starting Materials 1-Unsubstituted compound (II) | Sulfonyl halide (III) | Procedure | No. | Chemical structure | Physical constant | Yield (%) | C | H | N | S | Halogen |
|---|---|---|---|---|---|---|---|---|---|---|---|
| | | | | Produced 1-sulfonylimidazolidinedione (I) | | | Elementary analysis (%) | | | | |
| 2 | 33 | A | 62 | 3,5-diCl-C₆H₃-N(ring)-N-SO₂-n-C₁₂H₂₅ | M.P., 123.0–124.0° C | 76 | 52.83 (52.98) | 6.33 (6.29) | 5.87 (6.06) | 6.72 (6.65) | (Cl) 14.85 (15.01) |
| 2 | 42 | B | 63 | 3,5-diCl-C₆H₃-N(ring)-N-SO₂CH₂CH=CH₂ | M.P., 141.5–144.5° C | 79 | 41.28 (41.52) | 2.89 (3.01) | 8.02 (8.07) | 9.18 (8.99) | (Cl) 20.31 (20.43) |
| 3 | 23 | A | 64 | 3,5-diBr-C₆H₃-N(ring)-N-SO₂-n-C₃H₇ | M.P., 155.0–158.5° C | 85 | 32.75 (32.91) | 2.75 (2.88) | 6.37 (6.45) | 7.29 (7.13) | (Br) 36.31 (36.39) |
| 5 | 21 | A | 65 | 3,5-diCl-C₆H₃-N(ring)-N-SO₂CH₃, CH₃ | M.P., 184.0–186.0° C | 90 | 39.18 (39.39) | 2.99 (3.10) | 8.31 (8.26) | 9.51 (9.14) | (Cl) 21.03 (20.69) |
| 5 | 23 | A | 66 | 3,5-diCl-C₆H₃-N(ring)-N-SO₂-n-C₃H₇, CH₃ | M.P., 144.0–145.5° C | 92 | 42.75 (42.73) | 3.86 (4.02) | 7.67 (7.66) | 8.78 (8.72) | (Cl) 19.41 (19.53) |
| 6 | 21 | B | 67 | 3,5-diCl-C₆H₃-N(ring)-N-SO₂CH₃, (CH₃)₂ | M.P., 137.0–139.0° C | 85 | 41.04 (41.12) | 3.44 (3.48) | 7.98 (7.87) | 9.13 (8.88) | (Cl) 20.19 (20.32) |
| 6 | 22 | B | 68 | 3,5-diCl-C₆H₃-N(ring)-N-SO₂C₂H₅, (CH₃)₂ | M.P., 154.0–156.5° C | 79 | 42.75 (42.88) | 3.86 (3.89) | 7.67 (7.65) | 8.78 (8.69) | (Cl) 19.41 (19.40) |
| 6 | 23 | A | 69 | 3,5-diCl-C₆H₃-N(ring)-N-SO₂-n-C₃H₇, (CH₃)₂ | M.P., 139.0–140.5° C | 83 | 44.34 (44.29) | 4.25 (4.27) | 7.39 (7.38) | 8.45 (8.32) | (Cl) 18.70 (18.40) |
| 2 | 51 | A | 70 | 3,5-diCl-C₆H₃-N(ring)-N-SO₂CH₂CH₂CH₂Cl | M.P., 146.0–149.0° C | 85 | 37.37 (37.50) | 2.88 (2.96) | 7.26 (7.23) | 8.31 (8.20) | (Cl) 27.58 (27.49) |

EXAMPLE 2

Formulation of compositions a. Dust

2 Parts of the compound (55) and 98 parts of clay were thoroughly pulverized and mixed together to obtain a dust containing 2% of the active ingredient. In application, the dust was dusted as such.

b. Dust

2 Parts of the compound (57) and 98 parts of talc were thoroughly pulverized and mixed together to obtain a dust containing 2% of the active ingredient. In application, the dust was dusted as such.

c. Wettable powder

50 Parts of the compound (57), 5 parts of a wetting agent of the alkylbenzenesulfonate type and 45 parts of diatomaceous earth were thoroughly pulverized and mixed together to obtain a wettable powder containing 50% of the active ingredient. In application, the wettable powder was diluted with water, and the resulting solution was sprayed.

d. Emulsifiable concentrate

10 Parts of the compound (54), 80 parts of dimethyl sulfoxide and 10 parts of an emulsifier of the polyoxyethylene phenylphenol ether type were mixed together to obtain an emulsifiable concentrate containing 10% of the active ingredient. In application, the emulsifiable concentrate was diluted with water, and the resulting emulsion was sprayed.

e. Granule

5 Parts of the compound (66), 93.5 parts of clay and 1.5 parts of a binder of the polyvinyl alcohol type were thoroughly pulverized and mixed together, kneaded with water and then granulated and dried to obtain a granule containing 5% of the active ingredient.

The following examples show some typical test data supporting the excellent activity of the 1-sulfonylimidazolidinediones (I). In these examples, the compound numbers correspond to those in Table 1.

EXAMPLE 3

Test for *Pellicularia sasakii*-controlling effect on rice plants:

The test compound in the form of a dust preparation was applied to rice plants (variety: Wase-Asahi), cultured in porcelain Wagner pots (1/500 a) and grown up to a grass height of 50 to 60 cm, at a rate of 3 kg per 10 a by the use of a duster. After one day, a mycelial disc of *Pellicularia sasakii* was attached to the sheath of each stem for inoculation. Five days thereafter, the size of the diseased spot generated on the sheath was measured, and the degree of damage was calculated according to the following equation to estimate the disease-controlling effect of the compound.

$$\text{Degree of damage (\%)} = \frac{\text{Average length of diseased spot in treated plot}}{\text{Average length of diseased spot in untreated plot}} \times 100$$

The results are shown in Table 2.

Table 2

| Test compound | Concentration of active ingredient (%) | Degree of damage (%) |
| --- | --- | --- |
| 55 | 1.4 | 25 |
| 56 | 1.4 | 19 |
| 59 | 1.4 | 19 |
| 66 | 1.4 | 16 |
| Dust of Validamycin (commercially available fungicide) | as Validamycin A*) (0.30 %) | 31 |
| Untreated plot | — | 100 |

Note:
*)Antibiotic produced by Streptomyces hygroscopicus limone

EXAMPLE 4

Test for *Botrytis cinerea*-controlling effect on cucumbers:

An aqueous dilution of the test compound in the form of a wettable powder preparation was applied to cotyledons of cucumbers, cultered in pots of 9 cm in diameter and the first leaf was nipped off when it developed, at a rate of 7 ml per pot. After one day, agar discs (diameter: 5 mm) with *Botrytis cinerea* were attached to the leaves for inoculation. Three days thereafter, the disease severity was observed, and the disease-controlling effect was estimated.

The systemic activity of the test compound was tested by the water culture method in the following manner. The plants were pulled out from the pots carefully so as not to damage the roots, and the soil attached to the roots was well removed by water-washing. The plants were placed into flasks containing a 5 ppm solution of the test compound (50 ml) and allowed to stand for 3 days at a constant temperature under illumination. Agar discs with the mycelium were attached to the cotyledons for inoculation, and the degree of damage was examined three days thereafter.

Percentage of control was determined by the following procedure. The rate of diseased area on the tested leaf was measured and classified in one of the six infectious indexes (0, 1, 2, 3, 4, 5) according to the undermentioned criteria. The number of leaves corresponding to each infectious index ($n_0$, $n_1$, $n_2$, $n_3$, $n_4$, $n_5$) was determined, and calculation was effected according to the undermentioned equation.

| Infectious index | Rate of diseased area |
| --- | --- |
| 0 | No diseased spot |
| 1 | Diseased spot immediately under or around inoculated spot |
| 2 | Diseased spot in about 1/5 of leaf area |
| 3 | Diseased spot in about 2/5 of leaf area |
| 4 | Diseased spot in about 3/5 of leaf area |
| 5 | Diseased spot in more than 3/5 of leaf area |

Disease-preventing value (%) =

$$\left\{ 1 - \frac{0 \times n_0 + 1 \times n_1 + 2 \times n_2 + 3 \times n_3 + 4 \times n_4 + 5 \times n_5}{5 \times n} \right\} \times 100$$

The test for examining the effect of prevention of diseased spot-development was carried out in the following manner. An agar disc with the mycelium was attached to the first leaf for inoculation. After one day, the diameter of the diseased spot was measured. The solution of the test compound was applied to the plant at a rate of 7 ml per pot, and two days thereafter, the diameter of the diseased spot was again measured, and the effect for prevention of diseased spot-development was calculated according to the following equation:

Effect for prevention of diseased spot-development (%) =

$$\left\{ 1 - \frac{\text{Increase in length of infectious spot in treated plot}}{\text{Increase in length of infectious spot in untreated plot}} \right\} \times 100$$

The results are shown in Table 3.

| Infectious index | Rate of diseased area |
|---|---|
| 0 | No diseased spot |
| 1 | Diseased spot immediately under or around inoculated spot |
| 2 | Diseased spot in about 1/5 of leaf area |
| 3 | Diseased spot in about 2/5 of leaf area |
| 4 | Diseased spot in about 3/5 of leaf area |
| 5 | Diseased spot in more than 3/5 of leaf area |

Degree of damage (%) =
$$\frac{0 \times n_0 + 1 \times n_1 + 2 \times n_2 + 3 \times n_3 + 4 \times n_4 + 5 \times n_5}{5 \times n} \times 100$$

Table 3

| Test compound | Concentration of active ingredient (ppm) | Disease preventing effect | Systemic activity | Effect for prevention of diseased spot-development (%) |
|---|---|---|---|---|
| 55 | 50 | 100 | | |
|    | 5 | | 88 | |
|    | 100 | | | 88 |
| 56 | 50 | 100 | | |
|    | 5 | | 92 | |
|    | 100 | | | 78 |
| 57 | 50 | 98 | | |
|    | 5 | | 79 | |
|    | 100 | | | 65 |
| 58 | 50 | 100 | | |
|    | 5 | | 63 | |
|    | 100 | | | 73 |
| (structure 1: 3,5-dichlorophenyl imidazolidine-2,4-dione, NH) | 50 | 70 | | |
|    | 5 | | 0 | |
|    | 500 | | | 13 |
| (structure 2: 3,5-dichlorophenyl N-CO-C₂H₅ imidazolidinedione) | 50 | 89 | | |
|    | 5 | | 0 | |
|    | 500 | | | 21 |
| Methyl-1-(butylcarbamoyl)-2-benzimidazole carbamate (commercially available fungicide) | 50 | 90 | | |
|    | 5 | | 91 | |
|    | 500 | | | 87 |
| Untreated | — | 0 | 0 | 0 |

Note:
[1]Known fungicide as described in U.S. Pat. No. 3,668,217
[2]Known fungicide as described in U.S. Pat. No. 3,716,552

EXAMPLE 5

Test for *Sclerotinia sclerotiorum*-controlling effect on cucumbers

An aqueous dilution of the test compound in the form of a wettable powder preparation was applied to cucumbers, cultured in pots of 9 cm in diameter, when the first leaf was almost developed, at a rate of 7 ml per pot. After one day, *Sclerotinia sclerotiorum* was inoculated on the surface of the leaf, and the infectious state was examined three days thereafter. The degree of damage was determined in the following manner. The rate of infectious area on the leaf was measured and classified in one of the six infectious indexes (0, 1, 2, 3, 4, 5) according to the undermentioned criteria. The number of leaves corresponding to each infectious index ($n_0$, $n_1$, $n_2$, $n_3$, $n_4$, $n_5$) was determined, and calculation was effected according to the undermentioned equation.

The results are shown in Table 4.

Table 4

| Test compound | Concentration of active ingredient (ppm) | Degree of damage (%) |
|---|---|---|
| 54 | 100 | 12 |
| 55 | 100 | 0 |
| 56 | 100 | 0 |
| 57 | 100 | 0 |
| 63 | 100 | 9 |
| 64 | 100 | 0 |
| 66 | 100 | 3 |
| 70 | 100 | 0 |
| Methyl-1-(butylcarbamoyl)-2-benzimidazole carbamate fungicide)* | 100 | 32 |

Table 4-continued

| Test compound | Concentration of active ingredient (ppm) | Degree of damage (%) |
| --- | --- | --- |
| Untreated | — | 100 |

Note:
*Commercially available fungicide known as "Benomyl" (trade name: "Benlate")

EXAMPLE 6

Test for *Alternaria bracissicola*-controlling effect:

An aqueous dilution of the test compound in the form of a wettable powder preparation was applied to chinese cabbage (variety: Nozaki No. 2), cultured in pots of 9 cm in diameter and almost grown up to the two leaved stage, at a rate of 7 ml per pot. After one day, a spore suspension of *Alternaria bracissicola* was sprayed on the surface of the leaf for inoculation. The pots were left in a dark, moist room for one day and then under illumination for 2 days. Then, the infectious state was examined. The degree of damage was determined in the following manner. The rate of infectious area on the leaf was measured and classified in one of the infectious indexes (0, 1, 2, 3, 4, 5) according to the undermentioned criteria. The number of leaves corresponding to each infectious index ($n_0$, $n_1$, $n_2$, $n_3$, $n_4$, $n_5$) was determined, and calculation was effected according to the undermentioned equation.

| Infectious index | Rate of infectious area |
| --- | --- |
| 0 | No infectious spot |
| 1 | Infectious spot in less than 5% of leaf surface |
| 2 | Infectious spot in 5 to 30% of leaf surface |
| 4 | Infectious spot in 30 to 60% of leaf surface |
| 8 | Infectious spot in 60% or more of leaf surface |

Degree of damage (%) =
$$\frac{0 \times n_0 + 1 \times n_1 + 2 \times n_2 + 4 \times n_4 + 8 \times n_8}{8 \times n} \times 100$$

The results are shown in Table 5.

Table 5

| Test compound | Concentration of active ingredient (ppm) | Degree of damage (%) |
| --- | --- | --- |
| 53 | 200 | 11 |
|  | 100 | 7 |
| 54 | 200 | 2 |
|  | 100 | 5 |
| 55 | 200 | 0 |
|  | 100 | 0 |
| 57 | 200 | 0 |
|  | 100 | 1 |
| 69 | 200 | 6 |
|  | 100 | 21 |
| 70 | 200 | 1 |
|  | 100 | 2 |
| Polyoxin Al*) (commercially available fungicide) | 200 | 2 |
| Untreated | — | 100 |

Note: Antibiotic produced by *Streptomyces cacaoi*

EXAMPLE 7

Test for antimicrobial spectrum against industrial fungi

The effect for inhibition of hyphae growth was examined by the agar medium dilution method on *Aspergillus niger* ATCC 6275, *Cladosporium herbarum* IAM F 517 and *Chaetomium globosum* ATCC 6205 multiplying on industrial products and damaging them.

The results are shown in Table 6.

Table 6

| Test compound | Minimal inhibitory concentration of active ingredient (PPM) | | |
| --- | --- | --- | --- |
|  | A. Niger | C. herbarum | C. globosum |
| 59 | 1000 | 1000 | 1000 |
| 61 | 1000 | 2000 | 1000 |

What is claimed is:

1. A compound of the formula:

wherein X is a halogen atom, $R_1$ is a $C_1$–$C_{12}$ alkyl group, a $C_2$–$C_4$ alkenyl group or a halogenated $C_1$–$C_4$ alkyl group having 1 to 3 halogen atoms, and $R_2$ and $R_3$ are individually a hydrogen atom or a methyl group.

2. A compound according to claim 1, wherein X is a chlorine atom or a bromine atom.

3. A compound according to claim 1, wherein X is a chlorine atom or a bromine atom and $R_1$ is a $C_3$–$C_4$ alkyl group.

4. A compound according to claim 1, wherein $R_1$ is a mono-halogenated $C_3$–$C_4$ alkyl group.

5. A compound according to claim 1, wherein X is a chlorine atom or a bromine atom, $R_1$ is a $C_3$–$C_4$ alkyl group and each of $R_2$ and $R_3$ is a hydrogen atom.

6. A compound of the formula:

7. A compound of the formula:

8. A compound of the formula:

9. A compound of the formula:

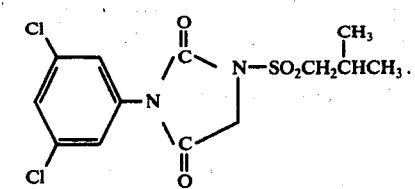

10. A compound of the formula:

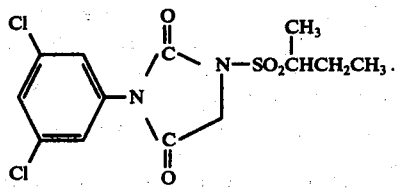

11. A compound of the formula:

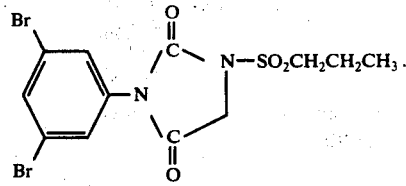

12. A compound of the formula:

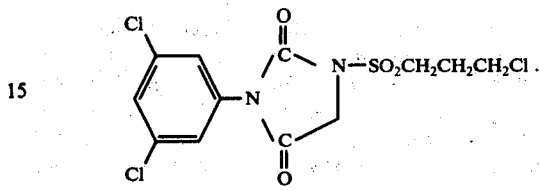

13. A microbicidal composition which comprises a microbicidally effective amount of a compound according to claim 1.

14. A microbicidal composition which comprises a microbicidally effective amount of a compound according to claim 1 and which is in the form of a dust, wettable powder, emulsifiable concentrate, granule, oil spray or aerosol.

15. A method for controlling fungi which comprises applying a fungicidally effective amount of a compound according to claim 1 to the fungi.

16. A method for controlling fungi which comprises applying a microbicidal composition which is in the form of a dust, wettable powder, emulsifiable concentrate, granule, oil spray or aerosol and containing a fungicidally effective amount of a compound according to claim 1 to the fungi.

* * * * *

UNITED STATES PATENT AND TRADEMARK OFFICE
CERTIFICATE OF CORRECTION

PATENT NO. : 4,056,622

DATED : November 1, 1977

INVENTOR(S) : Chiyozo Takayama et al

It is certified that error appears in the above–identified patent and that said Letters Patent are hereby corrected as shown below:

UNDER THE HEADING OF

"Attorney, Agent, or Firm" delete "Connolly and Hutz" and substitute therefor --Birch, Stewart, Kolasch and Birch--.

Signed and Sealed this

Twenty-fifth Day of July 1978

[SEAL]

Attest:

RUTH C. MASON
*Attesting Officer*

DONALD W. BANNER
*Commissioner of Patents and Trademarks*